US011540815B2

(12) United States Patent
Robinson et al.

(10) Patent No.: US 11,540,815 B2
(45) Date of Patent: Jan. 3, 2023

(54) CONNECTORS FOR ULTRASOUND IMAGING SYSTEM (71) Applicant: KONINKLIJKE PHILIPS N.V., Eindhoven (NL)

(72) Inventors: Andrew Lee Robinson, Kenmore, WA (US); Timothy Fred Nordgren, Bothell, WA (US); Scott Owen Schweizer, Snohomish, WA (US); Dennis Dean Clark, Lewistown, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 423 days.

(21) Appl. No.: 16/636,991

(22) PCT Filed: Aug. 9, 2018

(86) PCT No.: PCT/EP2018/071656
§ 371 (c)(1),
(2) Date: Feb. 6, 2020

(87) PCT Pub. No.: WO2019/030336
PCT Pub. Date: Feb. 14, 2019

(65) Prior Publication Data
US 2020/0367863 A1 Nov. 26, 2020

Related U.S. Application Data (60) Provisional application No. 62/640,623, filed on Mar. 9, 2018, provisional application No. 62/543,493, filed on Aug. 10, 2017.

(51) Int. Cl.
*A61B 8/00* (2006.01)
*H01R 13/514* (2006.01)

(52) U.S. Cl.
CPC ............ *A61B 8/56* (2013.01); *H01R 13/514* (2013.01); *H01R 2201/12* (2013.01)

(58) Field of Classification Search
CPC ........ A61B 8/56; A61B 8/565; H01R 13/502; H01R 13/514; H01R 2201/12
(Continued)

(56) References Cited

U.S. PATENT DOCUMENTS 4,726,230 A 2/1988 Yoshikawa et al.
5,443,070 A * 8/1995 Mniece ................. B06B 1/0622
600/447
(Continued)

FOREIGN PATENT DOCUMENTS

EP 1818012 A1 8/2007
EP 3056152 A1 8/2016
WO 2013038217 A1 3/2013

OTHER PUBLICATIONS

International Search Report and Written Opinion for International Application No. PCT/EP2018/071656, filed Aug. 9, 2018, 14 pages.

*Primary Examiner* — Khiem M Nguyen (57) ABSTRACT

Ultrasound imaging systems are provided. An ultrasound system according to some embodiments includes a console configured to selectively communicate with a first ultrasound imaging device and a second ultrasound imaging device. The console includes a housing, a computing device disposed within the housing, and a connector receptacle assembly coupled to the housing. The connector receptacle assembly includes a first connector bank including a first plurality of electrical connections; and a second connector bank including a second plurality of electrical connections. The connector receptacle assembly is selectively matable to a first connector of the first ultrasound imaging device via
(Continued)

only the first connector bank and to a second connector of the second ultrasound imaging device via the first and second connector banks.

10 Claims, 6 Drawing Sheets

(58) Field of Classification Search
USPC .................................. 600/437; 439/701, 709
See application file for complete search history.

(56) References Cited

U.S. PATENT DOCUMENTS

| | | | |
|---|---|---|---|
| 5,673,698 A | 10/1997 | Okada et al. | |
| 6,500,126 B1 | 12/2002 | Brock-Fisher | |
| 6,629,928 B1 | 10/2003 | Dolan et al. | |
| 2018/0289361 A1* | 10/2018 | Ledoux | A61B 8/4444 |
| 2020/0367863 A1* | 11/2020 | Robinson | A61B 8/56 |

* cited by examiner

CONNECTORS FOR ULTRASOUND IMAGING SYSTEM

RELATED APPLICATIONS

This application is the U.S. National Phase application under 35 U.S.C. § 371 of International Application No. PCT/EP2018/071656, filed on Aug. 9, 2018, which claims priority to and the benefit of both Provisional Application Ser. No. 62/640,623, filed Mar. 9, 2018 and Provisional Application Ser. No. 62/543,493, filed Aug. 10, 2017. These applications are hereby incorporated by reference herein.

TECHNICAL FIELD

The present disclosure relates generally to ultrasound imaging systems and, in particular, to connector receptacle assemblies and connectors of ultrasound imaging systems. For example, a connector receptacle assembly can include a first connector bank and a second connector bank and can be connected to a first connector via the first connector bank and to a second connector via the first and second connector banks.

BACKGROUND

Ultrasound imaging devices have become powerful and versatile diagnostic and interventional tools. Different types of probes can be used in breast imaging, cardiac imaging, vascular imaging, musculoskeletal imaging, and general imaging in internal medicine. Due to added functions and the increasing demand in performance of the ultrasound imaging devices, the number of electrical connections, or channels, in the connector increases as well. In addition, ultrasound imaging devices can include arrays of ultrasound elements and more channels in the connector translate into more array elements that can be addressed in an imaging event and therefore, faster scanning speed. While it is technically feasible to incorporate more channels in the connector, changing the connector interface on an ultrasound imaging system can be expensive and time-consuming. Every time a new connector interface is rolled out, the ultrasound imaging system manufacturer has to install new connectors not only on new systems but also on existing systems in the field.

SUMMARY

Embodiments of the present disclosure provide an ultrasound imaging system that selectively connects to a first ultrasound imaging device having a first connector and a second ultrasound imaging device having a second connector. The ultrasound imaging system includes a connector receptacle assembly that includes a first connector bank and a second connector bank. The connector receptacle assembly can connect to the first connector of the first ultrasound imaging device via only the first connector bank and to the second connector of the second ultrasound imaging device via both the first and second connector banks. In some embodiment, the ultrasound imaging system includes features that ensure secure and functional electrical communication with the first ultrasound imaging device or the second ultrasound imaging device. Aspects of the present disclosure advantageously provide an ultrasound imaging system with a connector interface that possesses both forward compatibility with new connectors of new ultrasound imaging devices and backward compatibility with existing or legacy connectors of existing or legacy ultrasound imaging devices.

In one embodiment, an ultrasound imaging systems is provided. The ultrasound system includes a console configured to selectively communicate with a first ultrasound imaging device and a second ultrasound imaging device. The console includes a housing, a computing device disposed within the housing, and a connector receptacle assembly coupled to the housing. The connector receptacle assembly includes a first connector bank including a first plurality of electrical connections; and a second connector bank including a second plurality of electrical connections. The connector receptacle assembly is selectively matable to a first connector of the first ultrasound imaging device via only the first connector bank and to a second connector of the second ultrasound imaging device via the first and second connector banks. In some embodiments, the ultrasound imaging system further includes the first ultrasound imaging device and the second ultrasound imaging device. In some embodiments, the first connector of the first ultrasound imaging device includes one connector module configured to couple to one of the first connector bank or the second connector bank, and the second connector of the second ultrasound imaging device includes two connector modules. In some implementations, the first connector bank and the second connector bank are spaced apart such that each of the first connector bank and the second connector bank is matable to the first connector and that both the first connector bank and the second connector bank are matable to the second connector.

In some embodiments, the first connector bank includes a first length and the second connector bank includes a second length parallel to the first length. In some instances, the first connector bank is surrounded by a first metal shield and the second connector bank is surrounded by a second metal shield. In some implementations, the first plurality of electrical connections includes a first socket and second socket and the second plurality of electrical connections includes a third socket and a fourth socket. In some embodiments, the computing device is configured to: identify properties of the first ultrasound imaging device and configure the first plurality of electrical connections of the first connector bank based on the identified properties of the first ultrasound imaging device, when the connector receptacle assembly is mated to the first connector of the first ultrasound imaging device via only the first connector bank; and identify properties of the second ultrasound imaging device and configure the first plurality of electrical connections of the first connector bank and the second plurality of electrical connections of the second connector bank based on the identified properties of the second ultrasound imaging device, when the connector receptacle assembly is mated to the second connector of the second ultrasound imaging device via the first and second connector banks. In some embodiments, the computing device is configured to disable the second connector bank of the connector receptacle assembly, when the connector receptacle assembly is mated to the first connector of the first ultrasound imaging device via only the first connector bank.

In another embodiment, an ultrasound imaging system is provided. The ultrasound imaging system includes a first imaging device including a first ultrasound imaging element at a distal portion and a first connector at a proximal portion; a second imaging device including a second ultrasound imaging element at a distal portion and a second connector at a proximal portion; a console including a housing, a computing device disposed within the housing, and a connector receptacle assembly coupled to the housing. In this embodiment, the connector receptacle assembly includes a first connector bank including a first plurality of electrical connections; and a second connector bank including a second plurality of electrical connections. In addition, in this embodiment, the connector receptacle assembly is configured to transfer electrical signals between the computing device and the first ultrasound imaging element to control imaging by the first imaging device when the first connector is mated to only the first connector bank, and the connector receptacle assembly is configured to transfer electrical signals between the computing device and the second ultrasound imaging element to control imaging by the second imaging device when the second connector is mated to the first connector bank and the second connector bank.

In some embodiments, the first connector includes one connector module configured to be matable to one of the first connector bank or the second connector bank and the second connector includes two connector modules configured to be matable to the first connector bank and the second connector bank respectively. In some implementations, the first connector bank includes a first length and the second connector bank includes a second length parallel to the first length. In some instances, the first connector bank is surrounded by a first metal shield and the second connector bank is surrounded by a second metal shield. In some embodiments, the computing device of the ultrasound imaging system is configured to identify properties of the first ultrasound imaging element and configure the first plurality of electrical connections of the first connector bank based on the identified properties of the first ultrasound imaging element, when the first connector is mated to only the first connector bank; and identify properties of the second ultrasound imaging element and configure the first plurality of electrical connections of the first connector bank and the second plurality of electrical connections of the second connector bank based on the identified properties of the second ultrasound imaging element, when the second connector is mated to the first connector bank and the second connector bank. In some embodiments, the computing device of the ultrasound imaging system is configured to disable the second connector bank of the connector receptacle assembly, when the first connector is mated to only the first connector bank.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
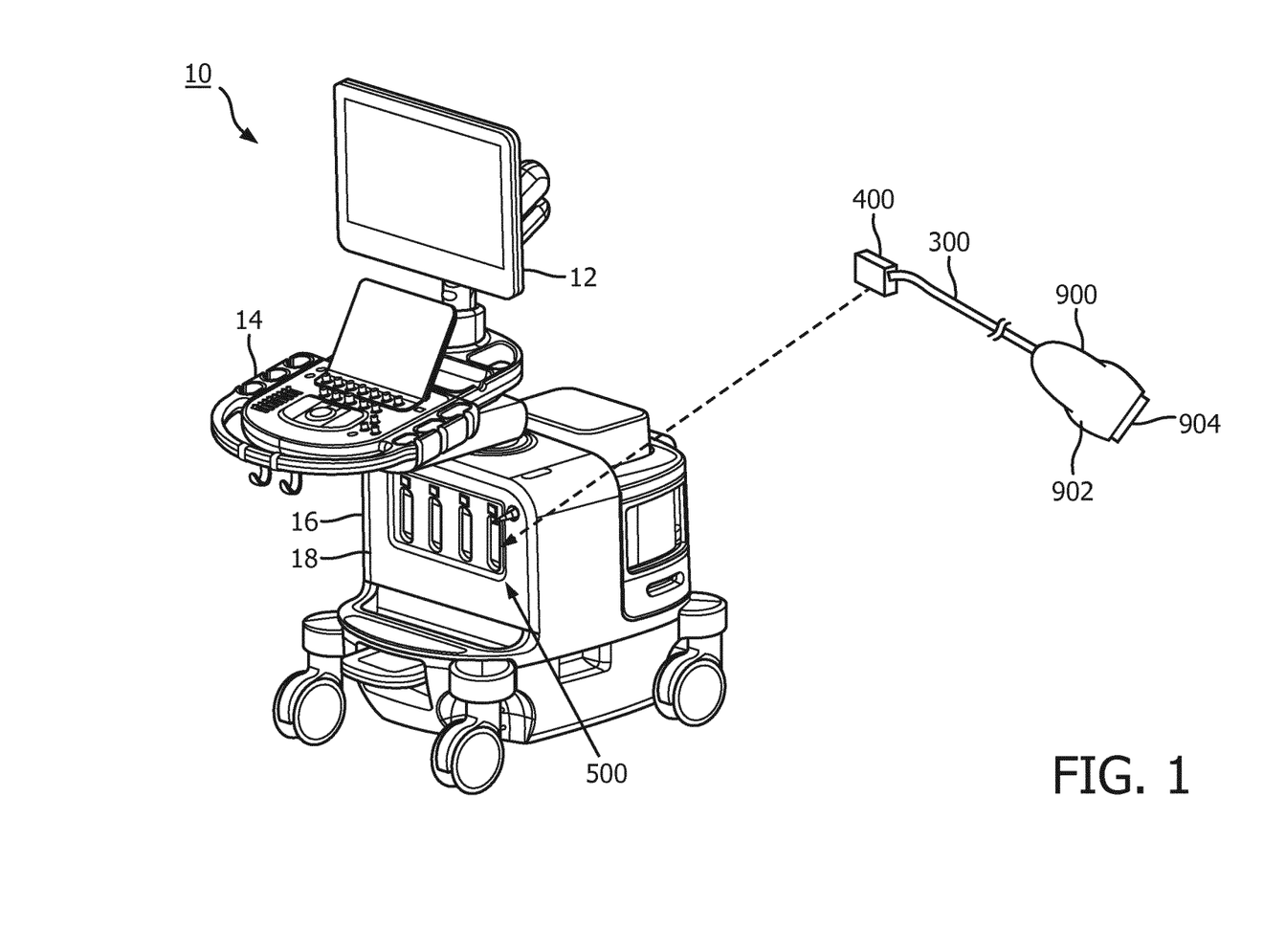
FIG. 1 is a diagrammatic perspective view of an ultrasound imaging system, according to aspects of the present disclosure.

FIG. 1 is a diagrammatic perspective view of an ultrasound imaging system 10, according to aspects of the present disclosure. An ultrasound imaging device 900 is connected to a cable 300 that is coupled to a connector 400. In various embodiments, the ultrasound imaging device 900 can be an external ultrasound probe, a transesophageal echocardiography (TEE) probe, an intracardiac echocardiography (ICE) probe, and/or an ultrasound imaging probe with therapy application functionalities. The ultrasound imaging device 900 includes a probe housing 902 and an ultrasound imaging element 904 on its distal portion. In some embodiments, the ultrasound imaging element 904 includes an ultrasound imaging array of a plurality of ultrasound transducers. In some embodiments, the plurality of ultrasound transducers can include capacitive micromachined ultrasound transducers (CMUT) or piezoelectric micromachined transducers (PMUT) or combinations thereof. One end of the cable 300 is connected to a proximal portion of the probe housing 902 and the other end is coupled to the connector 400.

In some embodiments, the ultrasound imaging device 900 is sized and shaped for positioning within the body of the patient, such as within the esophagus, heart, blood vessel, and/or other body lumen or cavity of the patient. In some embodiments, the ultrasound imaging device 900 is sized and shaped to be applied on the outside of the patient's body, such as with the ultrasound imaging element 904 in contact with the skin of the patient. The shape of the ultrasound imaging device 900 shown in FIG. 1 is only for illustration purposes and does not in any way limit the shapes, uses, types, and operations of the ultrasound imaging device 900 of the present disclosure.

In operation, the ultrasound imaging device 900 can obtain imaging data associated with the body of the patient. Electrical signals representative of the imaging data can be transmitted from the ultrasound imaging element 904 to the connector 400 along electrical conductors of the cable 300. The ultrasound imaging system 10 includes a console 16. The console 16 includes a housing 18 and a plurality of connector receptacle assemblies 500 on the housing 18. The connector 400 can engage one of the connector receptacle assemblies 500 such that the connector 400 is in electrical communication with the ultrasound imaging system 10. That way, the electrical signals can be transmitted from the ultrasound imaging device 900 to the ultrasound imaging system 10 via the connector 400 and the connector receptacle assembly 500. The ultrasound imaging system 10 includes one or more processors and/or memory forming a computing device that can process the electrical signals and output a graphical representation of the imaging data on a display device 12. The electrical conductors of the cable 300 and the connector 400 facilitate communication between the ultrasound imaging system 10 and the ultrasound imaging device 900. For example, a user of the ultrasound imaging system 10 can control imaging using the ultrasound imaging device 900 via a control interface 14 of the ultrasound imaging system 10. Electrical signals representative of commands from the ultrasound imaging system 10 can be transmitted to the ultrasound imaging device 900 via the connector 400 and the electrical conductors of the cable 300.

The connector 400 is configured to be insertable into the connector receptacle assembly 500 on the housing 18 of the console 16 of the ultrasound imaging system 10. The connector 400 and the connector receptacle assembly 500 can include any number of suitable electrical connections that are configured to electrically couple to one another. In some embodiments, the connector 400 houses one or more male or female zero insertion force (ZIF) connectors. In such embodiments, the connector receptacle assembly 500 includes corresponding female or male ZIF connectors. That way, when the connector 400 is inserted into the connector receptacle assembly 500, the male/female connectors in the connector 400 are electrically connected to the female/male connectors in the connector receptacle assembly 500. In other embodiments, the connector 400 houses one or more low insertion force (LIF) connectors, flat flexible connectors (FFCs), ribbon cable connectors, and serial advanced technology attachment (SATA) connectors. In those embodiments, the connector receptacle assembly 500 includes one or more corresponding connectors. In some embodiments, the electrical connections can be in the form of one or more sockets, each of which includes a plurality of electrical contacts. In a particular embodiment, the connector receptacle assembly 500 includes four male sockets and the connector 400 includes two or four female sockets. Each of the male sockets and a corresponding female socket include the same number of electrical contacts that are put in contact when the male connector socket is mated to the female socket. In some instances, each of the male/female sockets includes 100 to 150 electrical contacts.

Figure 2:
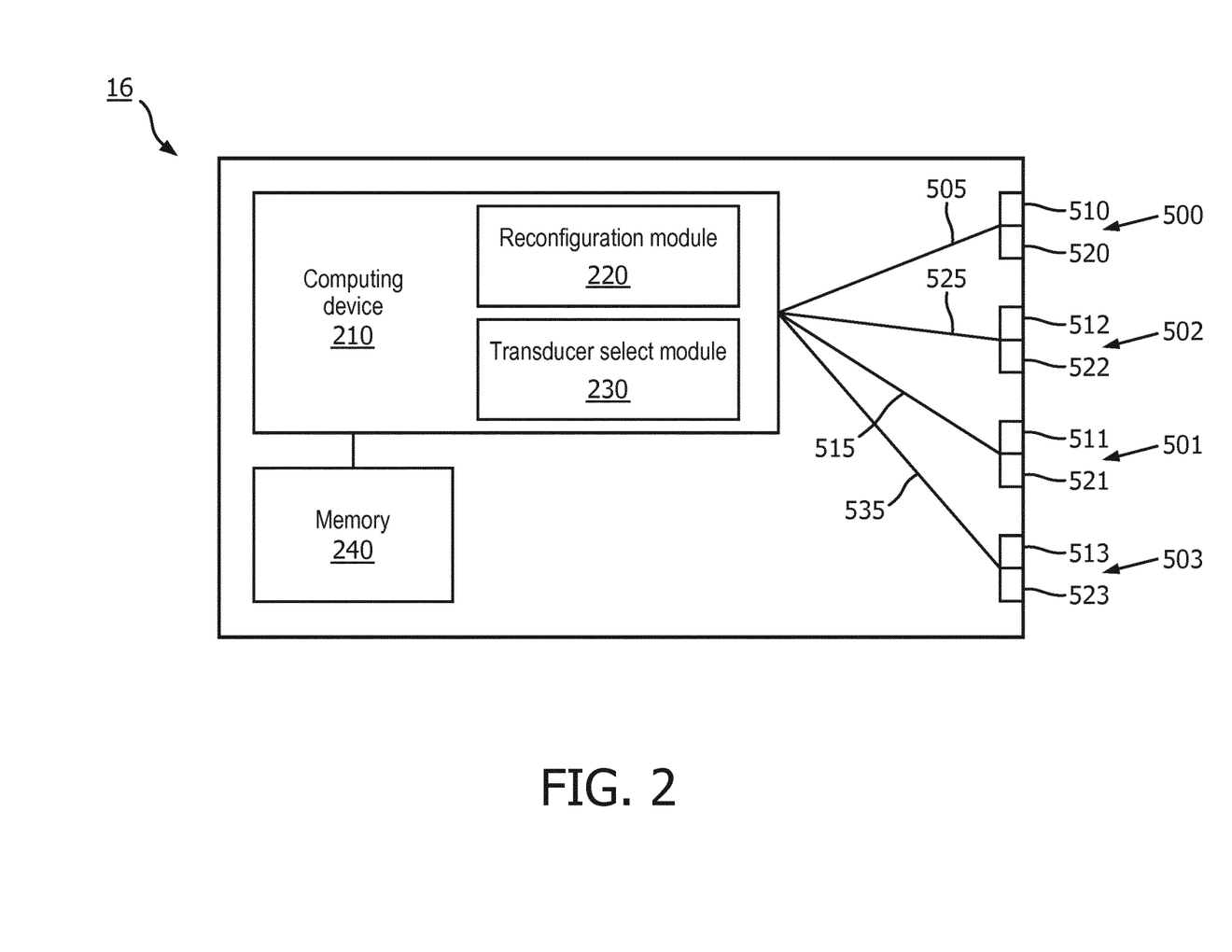
FIG. 2 is a schematic diagram of a computing device of the ultrasound imaging system, according to aspects of the present disclosure.

Referring to FIG. 2, illustrated therein is a schematic diagram of a computing device 210 positioned within the console 16 of the ultrasound imaging system 100. In some embodiments, the console 16 can include a plurality of connector receptacle assemblies 500. In the embodiment shown in FIG. 2, the console 16 includes four connector receptacle assemblies 500, 501, 502 and 503, each of which is in electrical communication with the computing device 210 via electrical cables. In some implementations, each connector receptacle assembly includes a first connector bank and a second connector bank. In the embodiments shown in FIG. 2, the connector receptacle assembly 500 includes a first connector bank 510 and a second connector bank 520; the connector receptacle assembly 501 includes a first connector bank 511 and a second connector bank 521; the connector receptacle assembly 502 includes a first connector bank 512 and a second connector bank 522; and the connector receptacle assembly 503 includes a first connector bank 513 and a second connector bank 523. In the embodiments shown in FIG. 2, the connector receptacle assemblies 500, 501, 502, and 503 are connected to the computing device 210 via cables 505, 515, 525, and 535. In some implementations, each of the cables includes two conductor bundles, one connecting to the first connector bank and the other connecting to the second connector bank.

In some embodiments, the computing device 210 can include a reconfiguration module 220. When a connector 400 of an ultrasound imaging device 900 is received by the connector receptacle assembly 500, the reconfiguration module 220 can identify the properties of the ultrasound imaging device 900, such as the type, the number of ultrasound transducers, signals transmitted through each electrical contact in the connector 400, and the active electrical contacts in the connector 400. Then the reconfiguration module 220 can configure the electrical connections between the connector 400 and the connector receptacle assembly 500 such that the computing device 210 can transmit and receive electrical signals to and from the ultrasound imaging device 900. In some embodiments, the computing device 210 is in communication with a memory 240. The memory 240 can store types of ultrasound imaging elements, properties of compatible ultrasound imaging devices, signals transmitted through each electrical contact in the connector, and the active electrical contacts in the connector. Once the reconfiguration module 220 of the computing device 210 identifies the properties of the connected ultrasound imaging device 900, the reconfiguration module 220 can compare the identified properties to the data stored in the memory 240 to determine the pattern and number of electrical connections for the connector receptacle assembly 500, including the pattern and number of electrical connections for the first connector bank 510 and the second connector bank 520, and reconfigure the electrical connections in the first and second connector banks 510 and 520 accordingly.

In some embodiments, the computing device 210 can include a transducer select module 230. When there are more than one connector receptacle assemblies 500 being connected to a connector of an ultrasound imaging device, the reconfiguration module 220 can identify all the connected ultrasound imaging devices and stored their identities either in a random access memory (RAM) or the memory 240. Based on the stored identified identities, the transducer select module 230 can select one or more of the connected ultrasound imaging devices and causes the computing device 210 to engage in electrical communication with the selected ultrasound imaging device(s). In some embodiments, the transducer select module 230 can select one or more of the connected ultrasound imaging devices in response to a user input or select one or more of the connected ultrasound imaging devices automatically when the computing device 210 enters into a specific state or mode. In some instances, when one connected ultrasound imaging device is selected by the transducer select module 230, the electrical connections to the other not selected ultrasound imaging devices are disabled.

Figure 3:
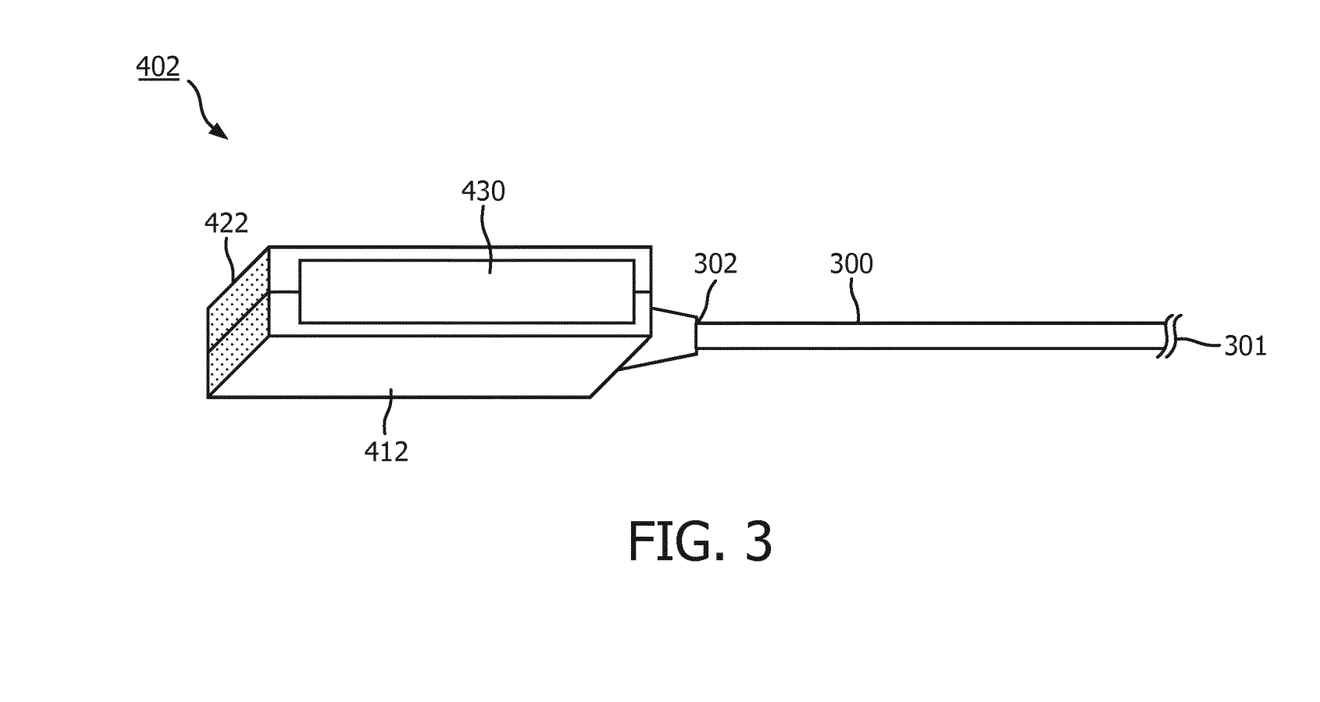
FIG. 3 is a diagrammatic perspective view of a connector and a cable, according to aspects of the present disclosure.

FIG. 3 is a diagrammatic perspective view of a connector 402 and a cable 300. The cable 300 has a distal end 301 that is connected to the ultrasound imaging device 900 (FIG. 1) and a proximal end 302 that is connected to the connector 402. The cable 300 can include one or more electrical conductors. In some embodiments, the connector 402 includes one connector module 430. The connector module 430 can include one or more electrical connectors. In some embodiment, the one or more electrical connectors include one or more male or female ZIF connectors. In other embodiments, the one or more electric connectors can be any suitable type of male or female electrical connector, such as LIF connectors, flat flexible connectors (FFCs), ribbon cable connectors, and serial advanced technology attachment (SATA) connectors. In embodiments represented by FIG. 3, the connector 402 includes a clam shell design with a first clam shell housing 412 and a second clam shell housing 422. In some other embodiments, the connector 402 can include a top housing away from the connector module 430 and a bottom housing with an opening to accommodate the connector module 430.

Figure 4:
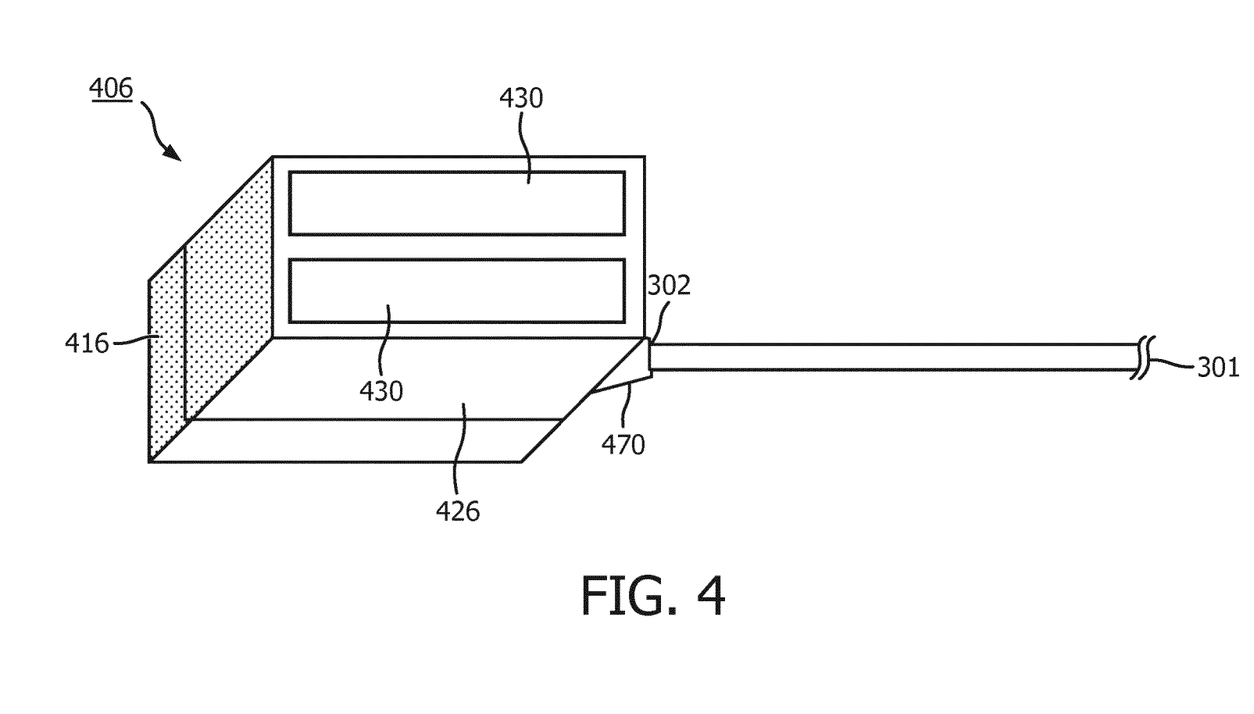
FIG. 4 is a diagrammatic perspective view of a connector and a cable, according to aspects of the present disclosure.

Referring now to FIG. 4, shown therein is a diagrammatic perspective view of a connector 406 and a cable 300. The cable 300 can include one or more electrical conductors. In some embodiments, the connector 406 includes two connector modules 430. Each of the two connector modules 430 can include one or more electrical connectors. Similar to the connector 402 shown in FIG. 3, the cable 300 has a distal end 301 that is connected to the ultrasound imaging device 900 (FIG. 1) and a proximal end 302 that is connected to the connector 406. The connector 406 includes a top housing 416, a bottom housing 426. In some embodiments, the top housing 416 and the bottom housing 426 define a chamber that may house space frames, frame halves, a plurality of printed circuit boards (PCBs), and/or other components. In some implementations, the top housing 416 may be fastened to the bottom housing 426 by fasteners or screws. In some embodiments, the connector 406 also includes a conical cable housing 470 that couples to the cable 300 at the proximal end 302 of the cable 300. The conical cable housing 470 can serve as a cable strain relief to reduce mechanical stress on the cable 300. The conical cable housing 470 may include a distal end and a proximal end. In some instances, the distal end of the conical cable housing 470 has a diameter smaller than the diameter of the proximal end. When the top housing 416 is fastened to the bottom housing 426, a gasket may be pressed between the top housing 416 and the bottom housing 426 to create a seal against ingress of fluids, such as bodily fluids, saline solutions, disinfectants, and enzymatic cleaning solutions. In some instances, metal particles are incorporated into gasket to shield the connector 406 from electromagnetic interferences. In some instances, the gasket also includes a ring-shaped portion to form a seal around a circumference of the proximal end of the conical cable housing 470. In some embodiments, the connector 406 can include a handle. The connector 406 is configured to be received in the connector receptacle assembly positioned on a console, such as the console 16. In some embodiments, the connector receptacle assembly may include a first connector bank and a second connector bank. In some embodiments, the first connector bank has a first length and the second connector bank has a second length. In those embodiments, the first length is parallel to the second length. In some embodiments, the connector 406 includes two halves, each of which includes a plurality of electrical contacts. In some implementations, each of the halves of the connector 406 includes two sockets. In some embodiments, one half is configured to be received in the first connector bank and the other half is configured to be received in the second connector bank. In some embodiments, the connector receptacle assembly may include a latching mechanism with a lever. Once activated by turning of the lever, the latching mechanism can secure the connector 406 to the connector receptacle assembly. In certain embodiments, the one or both of the connector modules 430 can be protected from gel or other material with a covering mechanism that is integrated into the connector 406. For example, a covering mechanism can be mounted to span the spacing in between the two connector modules, and in some instances the covering mechanism can be spring loaded such that when the connector 406 is removed from the connector receptacle assembly the covering mechanism will automatically cover one or more of the connector modules. Similarly, when the connector 406 is connected to the connector receptacle assembly the covering mechanism will spring open and can fit in between the two connector banks.

In some embodiments, the connector 406 includes one or more PCBs inside the chamber defined by the top housing 416 and the bottom housing 426. The PCBs can include one or more electronic components that provide signal conditioning and/or processing for the electrical signals representative of the imaging data obtained by the ultrasound imaging device 900 (FIG. 1). In some implementations, the connector 406 includes a plurality of PCBs. In some embodiment, the connector 406 may include one or more PCBs, such as 5 PCBs, disposed between the top housing 416 and the bottom housing 426. In some other embodiments, the connector 406 may include 4 PCBs. In some instances, the PCBs are planar and extend along planes parallel to one another.

Figure 5:
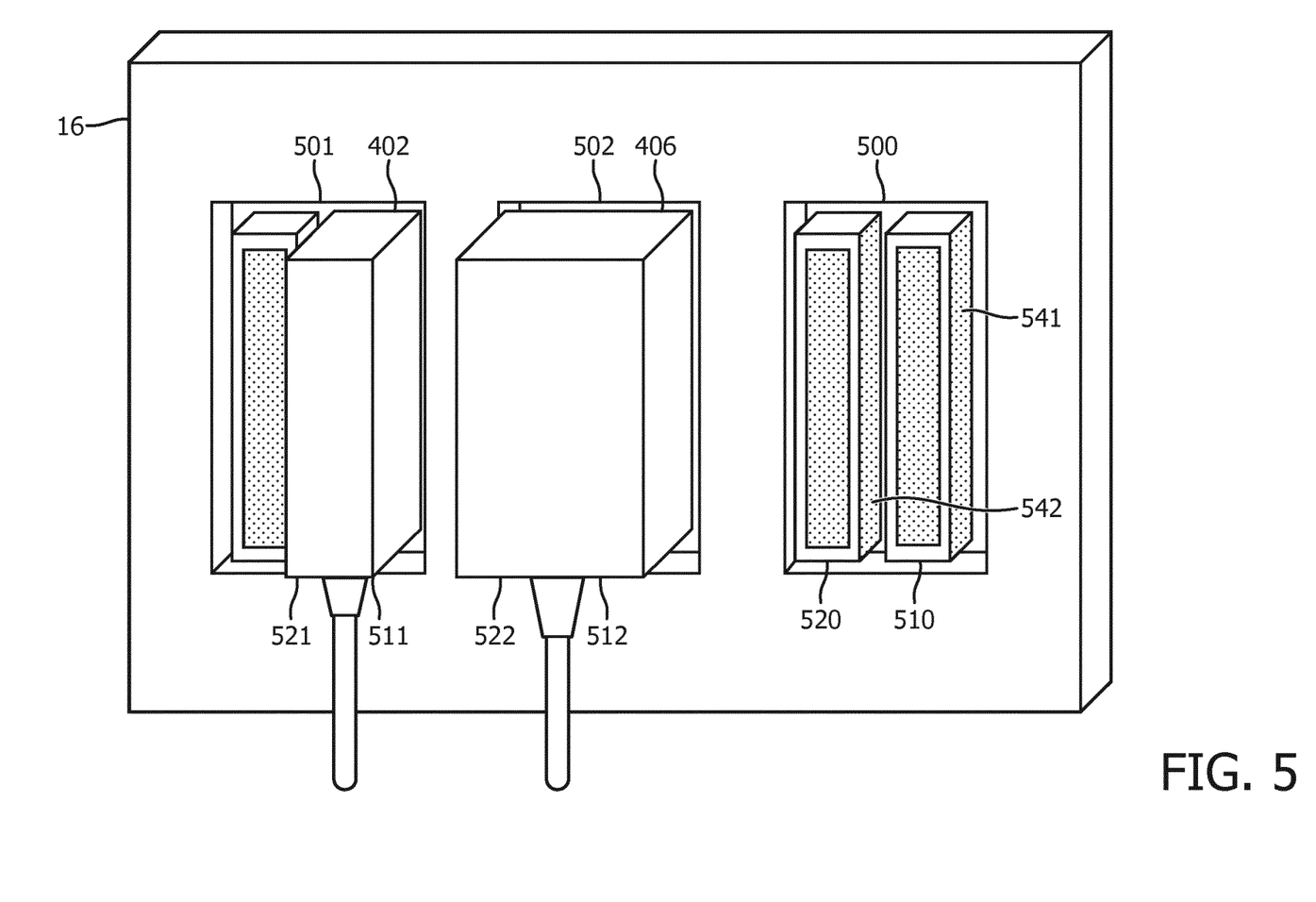
FIG. 5 is a diagrammatic perspective view of a first connector and a second connector mated to connector receptacle assemblies on a console of the ultrasound imaging system, according to aspects of the present disclosure.

FIG. 5 is a diagrammatic perspective view of a connector 402 and a connector 406 mated to connector receptacle assemblies 501 and 502 on the console 16 of the ultrasound imaging system 100 shown in FIG. 1. For the ease of reference, the connector 402, which is similar to the connector 402 shown in FIG. 3, may be referred to as the first connector 402; and the connector 406, which is similar to the connector 406 shown in FIG. 4, may be referred to as the second connector 406 herein. In addition, while all the connector receptacle assemblies 500, 501 and 502 on the console 16 are identical, the three connector receptacle assemblies shown in FIG. 5 are labeled and referred to as the connector receptacle assemblies 501, 502 and 500. As shown, the first connector 402 is mated to the connector receptacle assembly 501, the second connector 406 is mated to the connector receptacle assembly 502, and the connector receptacle assembly 500 is left open. Each of the connector receptacle assemblies 501, 502 and 500 includes two connector banks. The connector receptacle assembly 501 includes a first connector bank 511 and a second connector bank 521. The connector receptacle assembly 502 includes a first connector bank 512 and a second connector bank 522. The connector receptacle assembly 500 includes a first connector bank 510 and a second connector bank 520.

As shown in FIG. 5, the first connector 402 is mated to the connector receptacle assembly 501 via only the first connector bank 511, while the second connector bank 521 remains open. The second connector 406 is mated to the connector receptacle assembly 502 via both the first and second connector banks 512 and 522. In some instances, the first connector 402 can be referred to as a single-bank connector 402 because it is configured to mate to only one of the two banks of the connector receptacle assembly 501. The second connector 406 can be referred to a double-bank connector 406 because it is configured to mate to both connector banks 512 and 522 of the connector receptacle assembly 502. Conversely, the connector receptacle assemblies 500, 501 and 502, which are identical in these embodiments, can be referred to as including a partitioned interface because they are configured to engage a single-bank connector using one of its two connector banks or a double-bank connector using both of its connector banks. In other words, the connector receptacle assemblies 500, 501 and 502 are compatible with both single-bank and double-bank connectors.

In some embodiments, each of the connector banks 510, 520, 511, 521, 512, and 522 includes identical number of electrical connections. In some implementations, each of the connector banks includes two sockets and each socket includes 100 to 150 electrical contacts. That is, the second connector 406, with its ability to mate to the connector receptacle assembly 502 via both the first and second connector banks 512 and 522, has twice the capacity of the first connector 402, in terms of the number of electrical connections it can form with the connector receptacle assembly 502. In some instances, when the number of electrical connection required by an ultrasound imaging device is within the capacity of the first connector 402, the first connector 402 should be used as the connector for the ultrasound imaging device. In some other instances, when the number of electrical connection required by an ultrasound imaging device surpasses the capacity of the first connector 402, the second connector 406 should be used as the connector for the ultrasound imaging device. In some embodiments, the first connector 402 represents an existing or legacy connector of an existing or legacy ultrasound imaging device and the second connector 406 represents an expanded connector of a new or future ultrasound imaging device that requires more electrical connections. In those embodiments, the ultrasound imaging system 100 equipped with the connector receptacle assembly 500 of the present disclosure is compatible not only with the existing or legacy ultrasound imaging devices but also new and future ultrasound imaging devices. In other words, the ultrasound imaging system 100 equipped with the connector receptacle assembly 500 of the present disclosure possesses both forward and backward compatibility. That way, there will no longer be needs to constantly develop and install new connector receptacle assemblies on existing ultrasound imaging systems. It also eliminates the need to install multiple types of existing and new connector receptacle assemblies on new ultrasound imaging systems.

In some embodiments, when the first connector 402 is mated to the connector receptacle assembly 501 via the first connector bank 511, the reconfiguration module 220 (FIG. 2) can detect the engagement of the first connector 402 and identify the properties of the ultrasound imaging device connected to the first connector 402. In some implementations, the reconfiguration module 220 can disable the second connector bank 521, which is then not mated to any connector. In some other implementations, once the reconfiguration module 220 detects that the first connector bank 511 is mated to the first connector 402, it can send a signal to the transducer select module 230 and the transducer select module 230 can disable the second connector bank 521.

In embodiments represented by FIG. 5, the connector receptacle assembly 500 includes a first metal shield 541 that surrounds the first connector bank 510 and a second metal shield 542 that surrounds the second connector bank 520. The first and second metal shields 541 and 542 can shield off electromagnetic interference and improve the quality of electrical signals transmitted via the electrical connections between the connector receptacle assembly 500 and a connector mated thereto, such as the first connector 402 or the second connector 406. In some embodiments, the connector receptacle assembly 500 may be keyed to ensure correct connection to the first connector 402 and the second connector 406. In some implementations, the first metal shield 541 can include a first cutout portion and the second metal shield 542 can include a second cutout portion. The first cutout portion and the second cutout portion have different positions relative to the length and width of the respective connector bank. In these implementations, the first connector 402 can include a first protrusion, which is receivable within the first cutout portion when the first connector 402 is mated to the connector receptacle assembly 500. The first protrusion, however, is not receivable in the second cutout portion and prevents the first connector 402 from being received in the second connector bank 520. This cutout portion-protrusion pairing resembles a key and a corresponding lock and prevents a user from inadvertently connecting the first connector 402 to the second connector bank 520. In some alternative embodiments, the first and second metal shields 541 and 542 may include protrusions and the first and second connectors 402 and 406 may include corresponding cutout portions to achieve the same purpose preventing incorrect connections.

In some embodiments, the connector receptacle assembly 500 of the present disclosure includes a latching mechanism that includes a lever and a shaft. In some implementations, the latching mechanism can be activated by turning the lever either clockwise or counter-clockwise. The shaft can transfer the turning of the lever into a rotational movement of a retention force feature to grab on a portion of the first connector 402 or the second connector 406 to secure their engagement with the connector receptacle assembly 500. In some embodiments, the disclosed latching mechanism is operational both when the first connector 402 is mated to the connector receptacle assembly 501 via the first connector bank 511 and when the second connector 406 is mated to the connector receptacle assembly 502 via the first and second connector banks 512 and 522.

In some embodiment where the metal shields are not keyed to the connectors, the latching mechanism can include either an activation feature in the first connector bank or a deactivation feature in the second connector bank. In some embodiments where the activation feature is implemented in the first connector bank 511, when the first connector 402 is correctly mated to the first connector bank 511, the activation feature in the first connector bank 511 is mechanically activated and the latching mechanism is operable to secure the first connector 402. In those embodiments, when the first connector 402 is incorrectly mated to the second connector bank 521, the activation feature in the second connector bank 521 is not activated and the latching mechanism cannot secure the first connector 402 to the second connector bank 521. Still, in those embodiments, when the second connector 406 is mated to the connector receptacle assembly 502, the activation features in both the first connector bank 512 and the second connector bank 522 are mechanically activated and the latching mechanism is operable to secure the second connector 406 to the connector receptacle assembly 502. In some other embodiments where the deactivation feature is implemented to the second connector bank 521, when the first connector 402 is incorrectly mated to the second connector bank 521, the deactivation feature in the second connector bank 521 is mechanically activated and the latching mechanism is inoperable to secure the first connector 402. In those embodiments, when the first connector 402 is correctly mated to the first connector bank 511, the deactivation feature in the first connector bank 511 is not activated and the latching mechanism is operable to secure the first connector 402. Similarly, in those embodiments, when the second connector 406 is mated to the connector receptacle assembly 502, the deactivation features in the first and second connector banks 512 and 522 are not activated and the latching mechanism is operable to secure the second connector 406 to the connector receptacle assembly 502.

Figure 6:
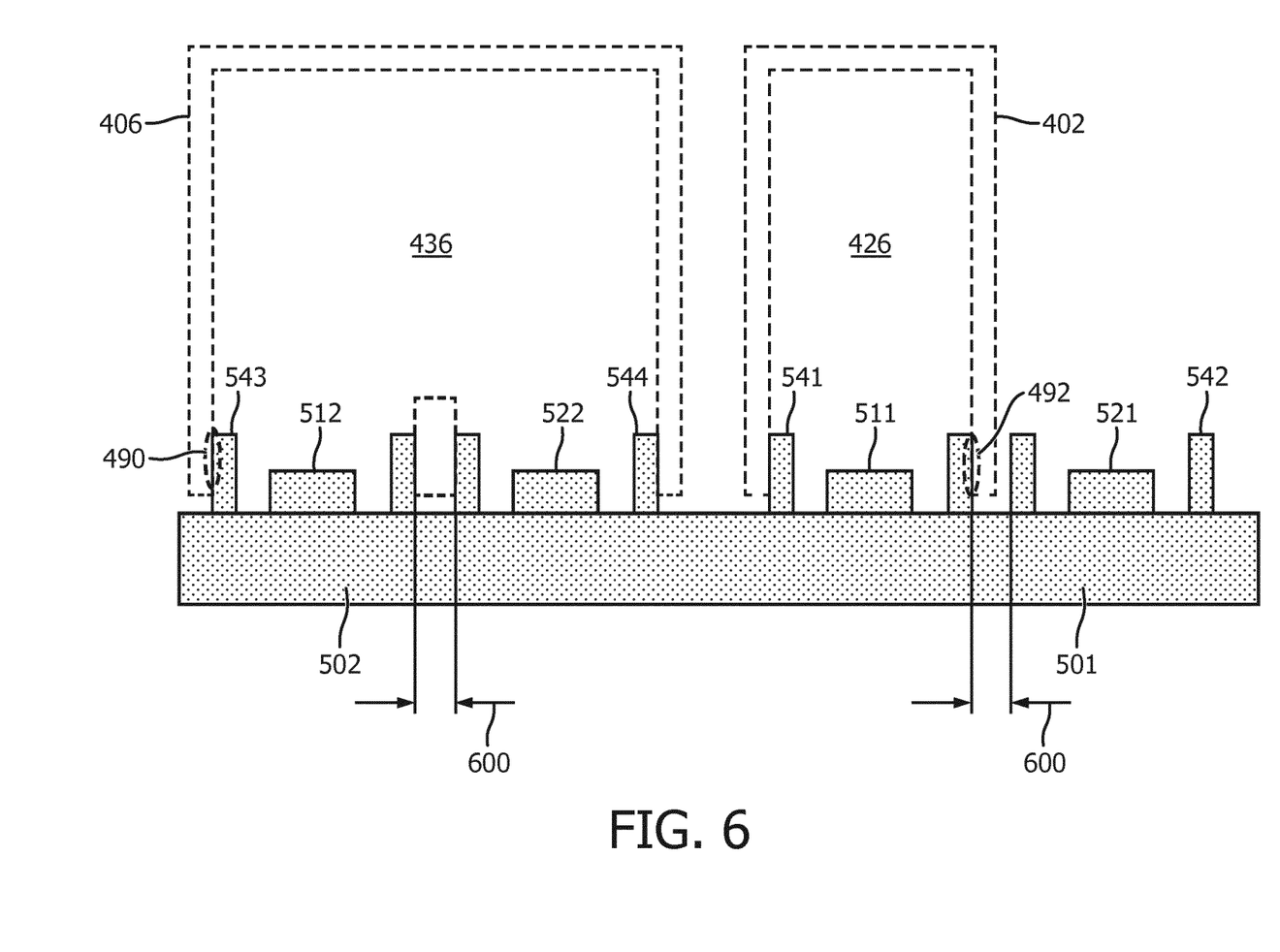
FIG. 6 is a diagrammatic cross sectional view of a first connector and a second connector connecting to connector receptacle assemblies on a console of the ultrasound imaging system, according to aspects of the present disclosure.

Referring now to FIG. 6, illustrated therein is a diagrammatic cross sectional view of the first connector 402 and the second connector 406 connecting to connector receptacle assemblies 501 and 502 of the ultrasound imaging system 100, according to aspects of the present disclosure. The first connector 402 is mated to the connector receptacle assembly 501 via only the first connector bank 511 and the second connector 406 is mated to the connector receptacle assembly 502 via the first and second connector banks 512 and 522. In some embodiments, the first connector 402 includes two PCBs in the chamber 426 defined by the housing while the second connector 406 includes four PCBs in the chamber 436 defined by the housing. In some other embodiments, the second connector 406 can include 5 PCBs in the chamber 436.

In some embodiments, the first connector 402 includes a first clam shell housing and a second clam shell housing. The first and second clam shell housings define a chamber that house a plurality of PCBs secured between the first and second clam shell housings. In some embodiments, the first connector bank 511 is parallel to and spaced part from the second connector bank 521 by a distance 600. The distance 600 is selected such that it can accommodate at least the thickness of one clam shell housings when the first connector 402 engages the first connector bank 511 and covers the second metal shield 541. In some other embodiments, the distance 600 is selected to accommodate twice the thickness of the first/second clam shell housing such that each of the first connector bank 511 and the second connector bank 521 can simultaneously mate to a first connector 402. In some embodiments, the first connector bank 511 includes a plurality of hooks that is part of the latching mechanism. In some implementations, the plurality of hooks is mechanically coupled to a lever. In some stances, the plurality of hooks is mechanically coupled to a shaft and the shaft is mechanically coupled to the lever. In some embodiments, turning of the lever rotates the shaft, which causes the plurality of hooks to grab onto a feature of the first connector 402, thereby securing the engagement between the first connector bank 511 and the first connector 402. In some embodiments, the plurality of hooks includes gears that engage one another or one or more common gears to devise a synchronized activation. That is, when the lever is turned to activate the latching mechanism, the turning or movement of all of the hooks is synchronized to evenly secure the engagement of the connector. The first connector bank 511 may also include a plurality of hooks that are mechanically coupled to a lever or a shaft. In some embodiments, turning of the lever not only activate the plurality of hooks in the second connector bank 521 but the plurality of hooks in the first connector bank 511.

In some embodiments, the lower edges 490 of the second connector 406 include one or more retention features that can exert force to maintain engagement of a connector, such as the first connector 402 or the second connector 406, to the connector receptacle assembly 500. In some embodiments, the retention feature includes a retention spring. In some implementations, the retention spring includes a first leg and a second leg. The first leg is curved and the second leg is planar. In some instances, the second leg of the retention spring is attached to the inner surface of the lower edge(s) 490 of the second connector 406 or the inner surface of the lower edge(s) 492 of the first connector 402. When the first/second connector 402/406 is mated to the connector receptacle assemblies 501 and 502, respectively, the retention spring is configured to press on the outer surface of the first metal shield 541/543 and/or the second metal shield 542/544. For ease of reference, the first metal shields 541, 543 and the second metal shields 542 and 544 can be collectively referred to as the metal shield 540. In those embodiments, the retention spring exerts a force normal to the outer surface of the metal shield 540 to serve as a means to retain the connector in addition to or in lieu of the latching mechanism described above. In some embodiments, the retention spring is made of beryllium copper (BeCu) alloy. Retention springs made of BeCu alloy has high mechanical strength, yet are non-magnetic and non-sparking. Retention springs made of BeCu also helps to further shield electromagnetic interferences that can raise the noise level in the electrical signals transferred using the electrical connections in the first/second connector 402/406 and the connector receptacle assembly 500.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
a first ultrasound imaging device comprising a first connector;
a second ultrasound imaging device comprising a single second connector, wherein the single second connector comprises:
a single housing;
a first connector module disposed within the single housing; and
a second connector module disposed within the single housing; and
a console configured to selectively communicate with the first ultrasound imaging device and the second ultrasound imaging device,
wherein the console comprises:
a housing;
a computing device disposed within the housing; and
a connector receptacle assembly coupled to the housing,
wherein the connector receptacle assembly comprises:
a first connector bank comprising a first plurality of electrical connections; and
a second connector bank comprising a second plurality of electrical connections,
wherein the connector receptacle assembly is selectively matable to the first connector of the first ultrasound imaging device via only the first connector bank or to the single second connector of the second ultrasound imaging device via both the first connector bank and second connector bank,
wherein, to mate the connector receptacle assembly to the single second connector of the second ultrasound imaging device, the first connector module is configured to couple to the first connector bank and the second connector module is configured to couple to the second connector bank.

2. The ultrasound imaging system of claim 1, wherein the first connector of the first ultrasound imaging device includes one connector module configured to couple to one of the first connector bank or the second connector bank.

3. The ultrasound imaging system of claim 2, wherein the first connector bank and the second connector bank are spaced apart such that each of the first connector bank and the second connector bank is matable to the first connector and that both the first connector bank and the second connector bank are matable to the second connector.

4. The ultrasound imaging system of claim 1, wherein the first connector bank comprises a first length and the second connector bank comprises a second length parallel to the first length.

5. The ultrasound imaging system of claim 1, wherein the first connector bank is surrounded by a first metal shield and the second connector bank is surrounded by a second metal shield.

6. The ultrasound imaging system of claim 1, wherein the first plurality of electrical connections comprises a first socket and second socket and the second plurality of electrical connections comprises a third socket and a fourth socket.

7. The ultrasound imaging system of claim 1, wherein the computing device is configured to:
when the connector receptacle assembly is mated to the first connector of the first ultrasound imaging device via only the first connector bank, identify properties of the first ultrasound imaging device and configure the first plurality of electrical connections of the first connector bank based on the identified properties of the first ultrasound imaging device; and
when the connector receptacle assembly is mated to the second connector of the second ultrasound imaging device via the first and second connector banks, identify properties of the second ultrasound imaging device and configure the first plurality of electrical connections of the first connector bank and the second plurality of electrical connections of the second connector bank based on the identified properties of the second ultrasound imaging device.

8. The ultrasound imaging system of claim 1, wherein the computing device is configured to:
when the connector receptacle assembly is mated to the first connector of the first ultrasound imaging device via only the first connector bank, disable the second connector bank of the connector receptacle assembly.

9. The ultrasound imaging system of claim 1, wherein:
the first imaging device comprising a first ultrasound imaging element at a distal portion and a first connector at a proximal portion;
the second ultrasound imaging device comprises a second ultrasound imaging element at a distal portion and the second connector at a proximal portion; and
the connector receptacle assembly is configured to transfer electrical signals between the computing device and the first ultrasound imaging element to control imaging by the first imaging device when the first connector is mated to only the first connector bank, and
the connector receptacle assembly is configured to transfer electrical signals between the computing device and the second ultrasound imaging element to control imaging by the second imaging device when the second connector is mated to the first connector bank and the second connector bank.

10. The ultrasound imaging system of claim 9, wherein the computing device is configured to:
when the first connector is mated to only the first connector bank, identify properties of the first ultrasound imaging element and configure the first plurality of electrical connections of the first connector bank based on the identified properties of the first ultrasound imaging element; and
when the second connector is mated to the first connector bank and the second connector bank, identify properties of the second ultrasound imaging element and configure the first plurality of electrical connections of the first connector bank and the second plurality of electrical connections of the second connector bank based on the identified properties of the second ultrasound imaging element.

* * * * *